US00PP10422P

United States Patent [19]

Lemon

[11] Patent Number: Plant 10,422

[45] Date of Patent: May 26, 1998

[54] VARIETY OF GERANIUM PLANT NAMED NAMED 'COTTON CANDY'

[75] Inventor: David Lemon, Lompoc, Calif.

[73] Assignee: John Bodger & Sons Company, So. El Monte, Calif.

[21] Appl. No.: 821,262

[22] Filed: Mar. 20, 1997

Related U.S. Application Data

[63] Continuation of Ser. No. 571,201, Dec. 12, 1995, abandoned.

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 5,374 12/1984 Schumann ..... Plt./87.12

*Primary Examiner*—Howard J. Locker

*Attorney, Agent, or Firm*—Fulwider Patton Lee Utecht, LLP

[57] ABSTRACT

The cultivar is characterized by its very dark foliage and medium salmon color flower. Its strong growth habit and free flowering provides for superb cuttings and also for quick recovery following wet weather conditions. The blooms are heat tolerant.

1 Drawing Sheet

BACKGROUND OF THE NEW PLANT

The present invention comprises a new and distinct cultivar of *Pelargonium* × *hortorum* known by the varietal name Cotton Candy (Oglevee No. 1283, Bodger No. 1GM 172-5). The new variety was discovered in a selective breeding program by David Lemon at Bodger Seeds, Ltd., Lompoc, Calif. The new variety is a selection from the crossing of Schone Helena (U.S. Plant Pat. No. 5,374) which is a salmon rose colored flower having medium green foliage with Eclipse Light Salmon (unpatented) which can be distinguished from the claimed cultivar by its light salmon color and by its light edged flower.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, 72° Fahrenheit vent temperature and grown in a soilless media of constant fertilizer 200–250 parts per million of nitrogen and potassium has a response time of six weeks from the rooted cutting to a flowering plant in a 10.0 cm pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted on approximately Feb. 18, 1995 and flowering on approximately Apr. 1, 1995 under full light and greenhouse, and colorings were taken indoors under 200–220 foot candles of fluorescent cool white light using the R.H.S. Colour Chart of The Royal Horticultural Society of London.

The Plant

Classification:

*Botanical.*—*Pelargonium×hortorum.*

Form: Semi-dwarf mound.

*Height.*—16.0–18.0 cm above the media surface.

*Growth.*—Free and early flowering.

*Strength.*—Free standing.

Foliage: Stalked leaf attachment.

Leaves:

*Size.*–8.5–10.0 cm across; fully expanded leaf.

*Shape.*—Reniform; cordate base.

*Margin.*—Crenate.

*Texture.*—Slightly pubescent; leathery.

*Color.*—Top: Green group 137A; Zone: Not present. True dark green leaves generally are not considered to have a zone, however due to stress or cultural conditions some appearance of a zone may occur. Bottom: Green group 137C.

*Ribs and veins.*—Palmate venation: Color: Yellow/green group 147B.

Petioles:

*Length.*—8.0–9.5 cm.

*Color.*—Green group 137B.

Stem:

*Color.* Yellow/Green group 146B.

*Internodes.*—1.0–2.5 cm in length.

The Bud

Shape: Upright; hemispherical cluster.

Size: 2.5–3.5 cm across.

Inflorescence

Blooming habit: Continuous blooming; semi-double; slow to shatter.

Size: 10.0–13.0 cm across.

Borne: Umbel; florets on pedicel; pedicel on peduncle; 6.0–9.0 cm above foliage.

Florets:

*Closed.*—Bud size: Width: 0.5–0.7 cm: Length: 0.8–1.0 cm; elliptical.

*Open.*—Form—Flat to slightly cupped; petaloids present; 29 florets per inflorescene. Color—Top: Red Group 38A on petals with veining of Red Group 39B. fading to Red Group 38B on outer edges; florets have white centers; Bottom petals: Red Group 39D. Petals—7–9 in number. Size—4.0–5.0 cm. Texture and appearance—Smooth and satiny; appearance from a distance is a clean medium salmon above dark green foliage.

Petaloids:

*Quantity.*—0–3 .

*Shape.*—Flat; distorted shape.

*Color.*—Top: Red group 38A fading to Red group 39B; Bottom: Red group 39D.

Pedicel:

*Length.*—3.0–3.5 cm .

*Color.*—Greyed/purple group 183B.

Peduncle: Arises from the node opposite the leaf petiole.

*Length.*—15.0–17.0 cm.

*Color.*—Yellow/green group 146B with occasional shadings of Greyed/purple group 183B.

Persistence:

*Disease resistance.*—Not known.

*Lasting quality.*—Slow to shatter; holds up exceptionally well when exposed to outdoor conditions.

Reproductive Organs

Stamens:

*Anthers.*—2.0–2.5 mm in length.

*Filaments.*—Length: 8.0–9.0 mm; Color: white with pink tips.

*Pollen.*—Golden brown.

Pistils:

*Number.*—One.

*Length.*—6.5–7.5 mm.

*Stigma.*—Color: Red/purple group 60C; 5–6 parted.

*Style.*—Length: 3.0–4.0 mm; Color: Red/purple group 60C.

Ovaries: Color: Light green; pubescent; Length: 5.0–6.0 mm.

Fruit: None.

General Characteristics

Cotton Candy is a distinctive new variety with medium salmon bloom and dark green foliage. The very dark green foliage is unique in the Geranium market and the medium salmon flower creates a very dramatic contrast. Cotton Candy is more compact than a green leaf zonal Geranium allowing for more pots per given area for efficient product finishing. Cutting production and rooting times are both acceptable. Outdoor performance is outstanding in high heat and the variety is quick to recover after wet weather. Given all these positive properties, this variety should please both the grower and gardener alike.

I claim:

1. A new and distinct variety of Geranium plant, substantially as shown and described.

* * * * *

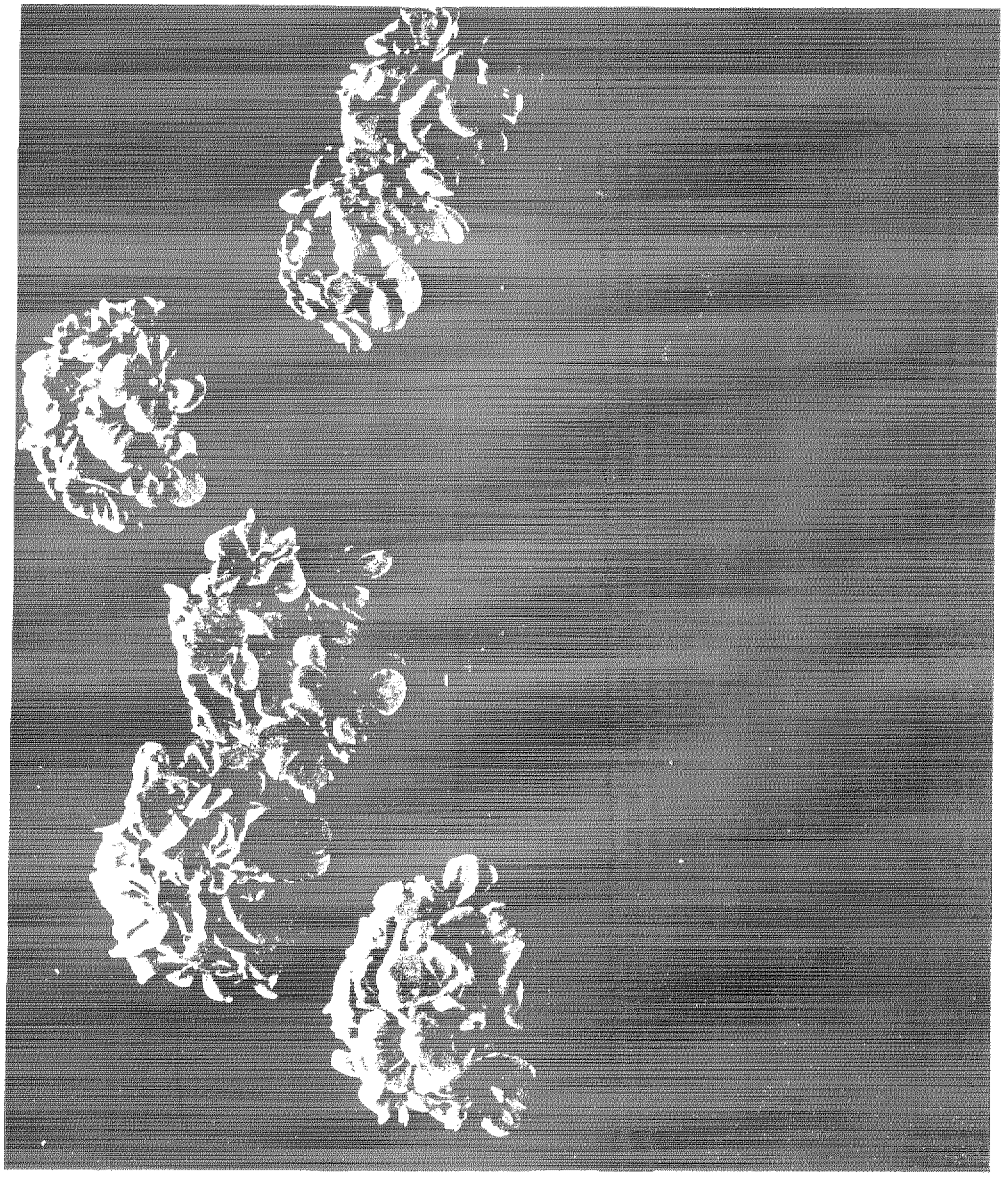

PLT-328 SR
C5203 OR PP 010,422
U.S. Patent May 26, 1998 Plant 10,422